(12) United States Patent
Hayashi (10) Patent No.: US 10,716,458 B2
(45) Date of Patent: Jul. 21, 2020

(54) ENDOSCOPIC SYSTEM, IMAGE PROCESSING DEVICE, IMAGE PROCESSING METHOD, AND PROGRAM

(71) Applicant: SONY CORPORATION, Tokyo (JP)

(72) Inventor: Tsuneo Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 300 days.

(21) Appl. No.: 15/113,089

(22) PCT Filed: Jan. 23, 2015

(86) PCT No.: PCT/JP2015/000297
§ 371 (c)(1),
(2) Date: Jul. 21, 2016

(87) PCT Pub. No.: WO2015/115073
PCT Pub. Date: Aug. 6, 2015

(65) Prior Publication Data
US 2017/0027416 A1    Feb. 2, 2017

(30) Foreign Application Priority Data
Jan. 30, 2014    (JP) .................................. 2014-015575

(51) Int. Cl.
| A61B 1/00 | (2006.01) |
| A61B 34/00 | (2016.01) |
| A61B 1/313 | (2006.01) |
| A61B 17/00 | (2006.01) |
(Continued)

(52) U.S. Cl.
CPC ...... *A61B 1/00009* (2013.01); *A61B 1/00078* (2013.01); *A61B 1/00147* (2013.01); *A61B 1/00154* (2013.01); *A61B 1/00174* (2013.01); *A61B 1/3132* (2013.01); *A61B 17/00234* (2013.01); *A61B 17/3423* (2013.01);
(Continued)

(58) Field of Classification Search
CPC .................................................. A61B 1/00009
See application file for complete search history.

(56) References Cited

U.S. PATENT DOCUMENTS

2009/0262186 A1* 10/2009 Tabata ..................... A61B 1/05
                                                    348/76
2010/0016666 A1    1/2010 Hasegawa
2012/0130168 A1    5/2012 Konomura
(Continued)

FOREIGN PATENT DOCUMENTS

EP    2 130 479 A1    12/2009
JP    5-49599 A        3/1993
(Continued)

OTHER PUBLICATIONS

Office Action dated Jan. 10, 2017 in Japanese Patent Application No. 2014-015575.
(Continued)

*Primary Examiner* — Alexandra L Newton
(74) *Attorney, Agent, or Firm* — Xsensus LLP (57) ABSTRACT

To solve the above problem, a first technology is an image processing device configured to estimate an approximate center of rotation of an endoscopic device based on motion detection in response to a movement of an objective lens at a distal portion of the endoscopic device by manipulating a proximal portion of the endoscopic device.

10 Claims, 11 Drawing Sheets

(51) Int. Cl.
  *A61B 17/34* (2006.01)
  *A61B 34/20* (2016.01)
(52) U.S. Cl.
  CPC ...... *A61B 34/75* (2016.02); *A61B 2034/2055* (2016.02); *A61B 2034/2065* (2016.02)

(56) References Cited

U.S. PATENT DOCUMENTS

2013/0165753 A1* 6/2013 Takahashi ................ A61B 1/05
                                                               600/109
2014/0036101 A1   2/2014 Imanishi

FOREIGN PATENT DOCUMENTS

| JP | 2008-80115 | 4/2008 |
| JP | 2013-192773 | 9/2013 |
| WO | 2012/141193 A1 | 10/2012 |

OTHER PUBLICATIONS

Office Action dated Jan. 29, 2018 in European Patent Application 15 704 390.2.
International Search Report dated Apr. 23, 2015 in PCT/JP2015/000297 filed Jan. 23, 2015.

\* cited by examiner

ENDOSCOPIC SYSTEM, IMAGE PROCESSING DEVICE, IMAGE PROCESSING METHOD, AND PROGRAM

TECHNICAL FIELD

The present disclosure relates to an endoscopic system, an image processing device, an image processing method, and a program, and particularly, for example, to an endoscopic system, an image processing device, an image processing method, and a program adapted to correct image shake in an image taken by an endoscopic device which is used in laparoscopic operations and the like.

CROSS REFERENCE TO RELATED APPLICATIONS

This application claims the benefit of Japanese Priority Patent Application JP 2014-015575 filed Jan. 30, 2014, the entire contents of which are incorporated herein by reference.

BACKGROUND ART

In recent years, in medical practice, laparoscopic operations may be performed instead of laparotomies in the related art.

Figure 1:
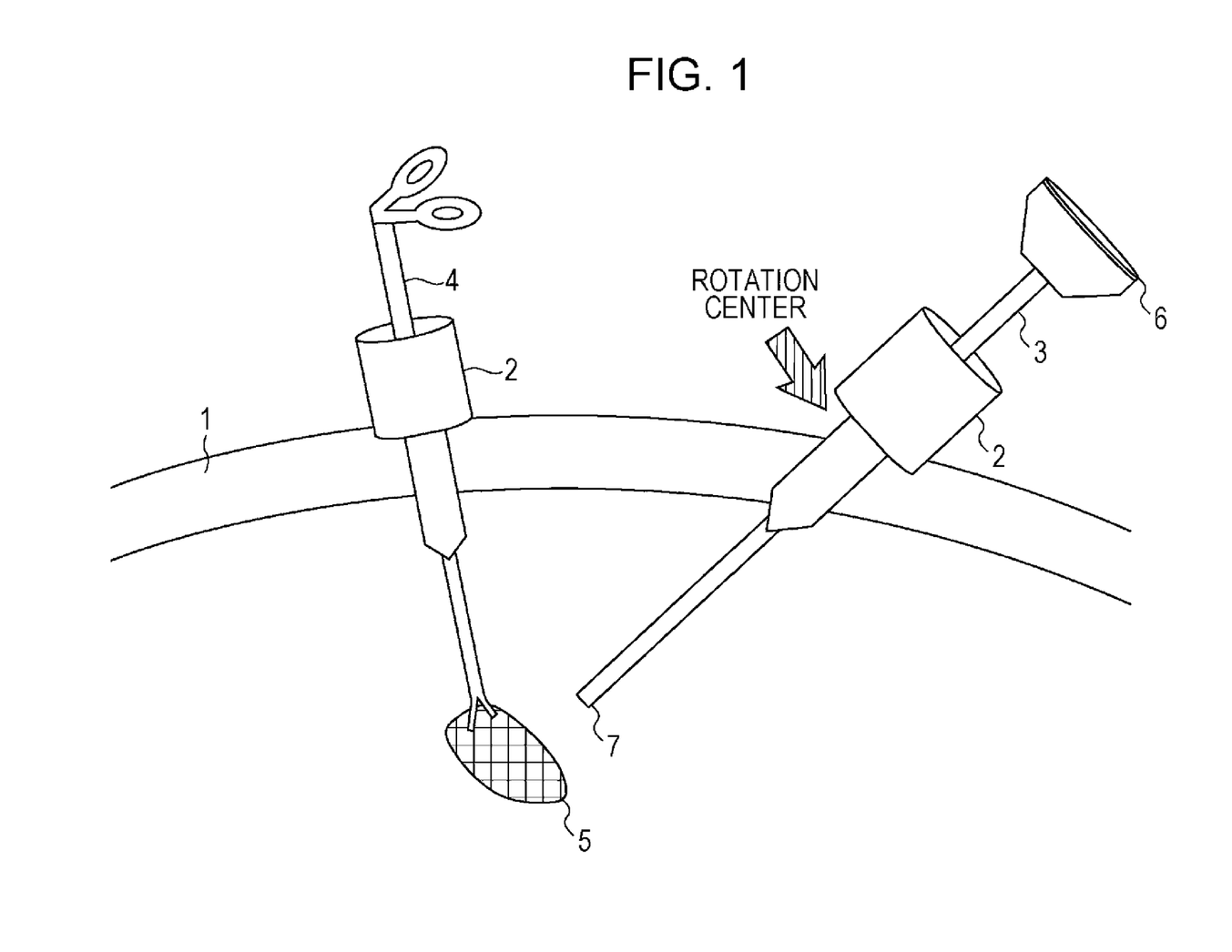
FIG. 1 is a diagram showing an outline of a laparoscopic operation.

FIG. 1 shows an outline of a laparoscopic operation. In the laparoscopic operation, for example, when an abdominal operation is performed, several opening tools, called trocars 2, are attached to an abdominal wall instead of performing a laparotomy, which has been hitherto performed, by cutting the abdominal wall 1, and a laparoscope (hereinafter, also referred to as an endoscopic device or an endoscope) 3 and a processing tool 4 are inserted into a body from holes provided in the trocars 2. While viewing an image of an affected part (a tumor or the like) 5 taken by the endoscope 3, a process such as excising the affected part 5 using the processing tool 4 is performed.

Since image shake may occur in the image taken by the endoscope 3, it is necessary to provide a mechanism for correcting the image shake.

For example, PTL 1 discloses an endoscope capable of adjusting an image taking position by bending a tip end part, and also discloses that a bending direction and a bending angular velocity of the tip end part are detected to correct shake based on the bending direction and the bending angular velocity.

CITATION LIST

Patent Literature

PTL 1: Japanese Unexamined Patent Application Publication No. 5-49599

SUMMARY OF INVENTION

Technical Problem

In the endoscope 3 having a linear rod shape as shown in FIG. 1, a head part 6 is held by an operator, an assistant, a scopist, a robot, or the like. However, when a hand or the like holding the head part 6 is shaken, the motion of the shake is transmitted to an objective lens 7 with the trocar 2 acting as a support (rotation center), and thus image shake may occur due to the shake of the hand holding the head part 6. In the related art, a gyro has been built in the head part 6 to detect a moving angular velocity thereof, but this moving angular velocity is used to detect a direction of a camera necessary for realizing, for example, three-dimensional display, and is not used in the correction of the image shake.

It is desirable to correct an image based on an angular velocity of a head part.

Solution to Problem

To solve the above problem, a first technology is an image processing device configured to estimate an approximate center of rotation of an endoscopic device based on motion detection in response to a movement of an objective lens at a distal portion of the endoscopic device by manipulating a proximal portion of the endoscopic device.

Advantageous Effects of Invention

According to the first and second embodiments of the present disclosure, it is possible to correct an image taken by the endoscopic device based on the angular velocity of the head part of the endoscopic device.

DESCRIPTION OF EMBODIMENT

Hereinafter, the best modes for carrying out the present disclosure (hereinafter, referred to as embodiments) will be described in detail with reference to the drawings.

Example of Configuration of Endoscopic System

Figure 2:
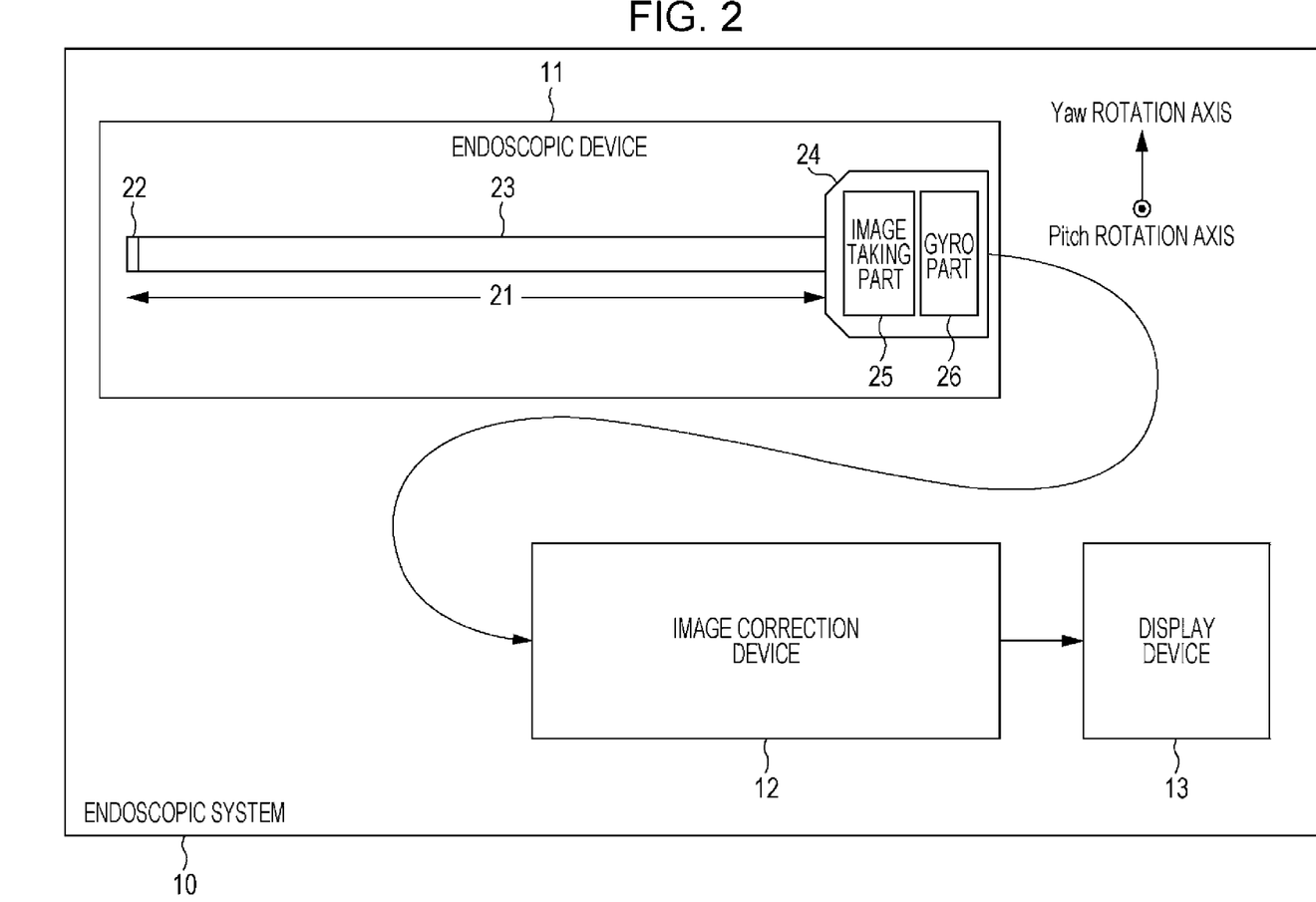
FIG. 2 is a block diagram showing an example of a configuration of an endoscopic system to which the present disclosure is applied.

FIG. 2 shows an example of a configuration of an endoscopic system according to an embodiment of the present disclosure. This endoscopic system 10 includes an endoscopic device 11, an image correction device (image processing device) 12, and a display device 13.

The endoscopic device 11 and the image correction device 12 may be connected to each other through a cable or wirelessly. In addition, the image correction device 12 may be disposed at a position separated from an operating room and be connected through a network such as local LAN or the Internet. The image correction device 12 and the display device 13 are connected to each other in the same manner.

The endoscopic device 11 includes a tube part 21 having a linear rod shape and a head part 24. The tube part 21 is also referred to as an optical visual tube or a hard tube, and the length thereof is approximately several tens of cm. At one end on the body insertion side thereof, an objective lens 22 is provided, and the other end is connected to the head part 24. An optical lens part 23 of a relay optical system is provided inside the tube part 21. The shape of the tube part 21 is not limited to the linear rod shape.

The head part 24 has an image taking part 25 and a gyro part 26 built therein. The image taking part 25 has an image taking element such as a CMOS and converts an optical image of an affected part input from the tube part 21 into an image signal at a predetermined frame rate.

The gyro part 26 detects an angular velocity at the time when the head part 24 is moved (a Yaw angular velocity $w_y$ with respect to a Yaw rotation axis and a Pitch angular velocity $w_p$ with respect to a Pitch rotation axis), and outputs the result of the detection to the downstream image correction device 12.

In the endoscopic device 11, the optical image of the affected part converged by the objective lens 22 enters the image taking part 25 of the head part 24 through the optical lens part 23, is converted into an image signal of a predetermined frame rate by the image taking part 25, and is output to the downstream image correction device 12. In addition, in the endoscopic device 11, the gyro part 26 detects a moving angular velocity of the head part 24, and outputs the result of the detection to the downstream image correction device 12.

Figure 3:
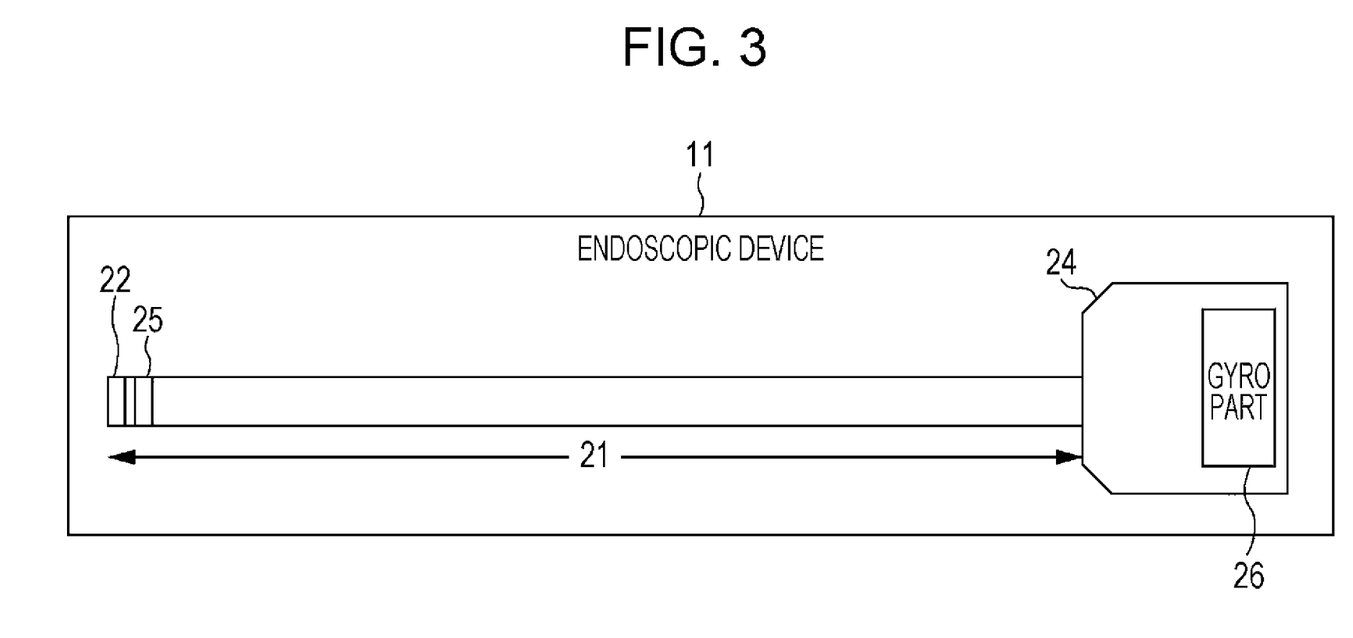
FIG. 3 is a block diagram showing another example of a configuration of an endoscopic device of FIG. 2.

FIG. 3 shows another example of the configuration of the endoscopic device 11. As shown in FIG. 3, the image taking part 25 may be disposed immediately after the objective lens 22 and the optical lens part 23 inside the tube part 21 may be omitted.

Figure 4:
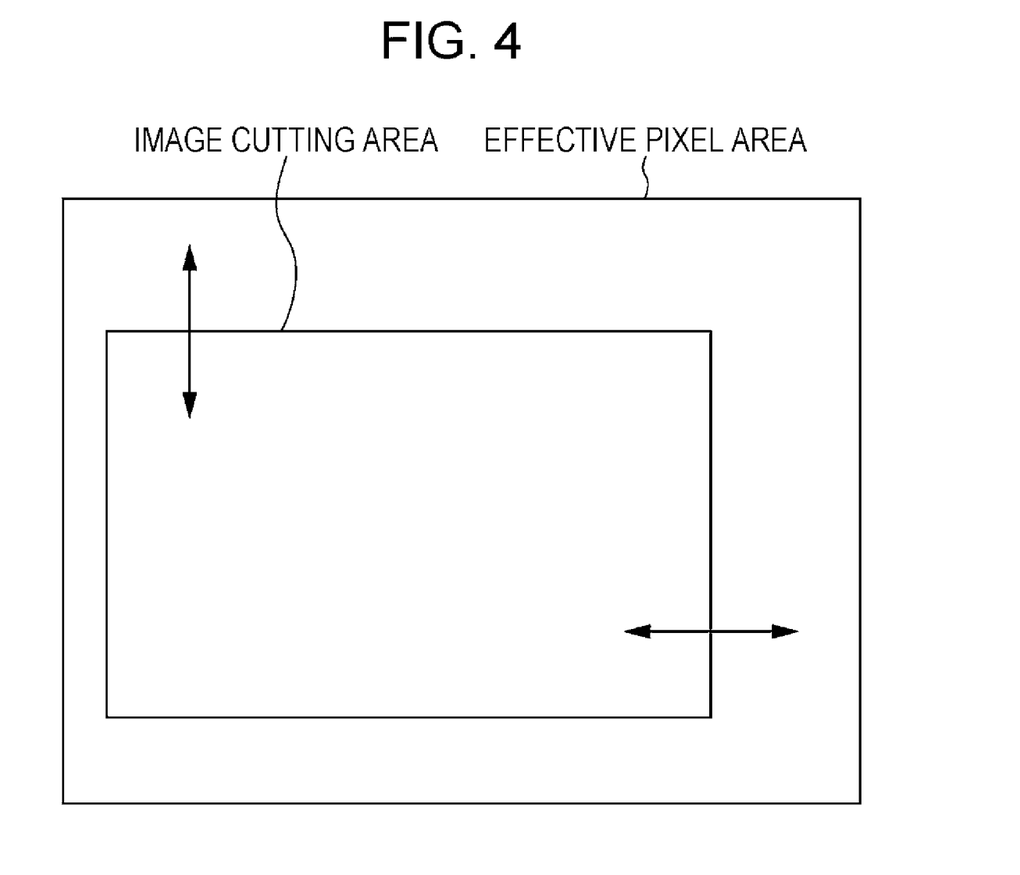
FIG. 4 is a diagram illustrating an outline of a correction process of an image correction device.

Next, FIG. 4 shows an outline of a correction process of the image correction device 12. The image correction device 12 outputs, to the downstream display device 13, an image signal which is obtained by cutting, from an entire region (effective pixel area) of an image signal input at a predetermined frame rate from the image taking part 25 of the endoscopic device 11, a cutting area having a smaller size than the effective pixel area. At this time, hand shake can be corrected by moving the position of the cutting area by a shift amount corresponding to the hand shake. In addition, when a shutter mechanism of the image taking part 25 of the endoscopic device 11 is a rolling shutter, a rolling shutter distortion occurring due to this can be removed.

Figure 5:
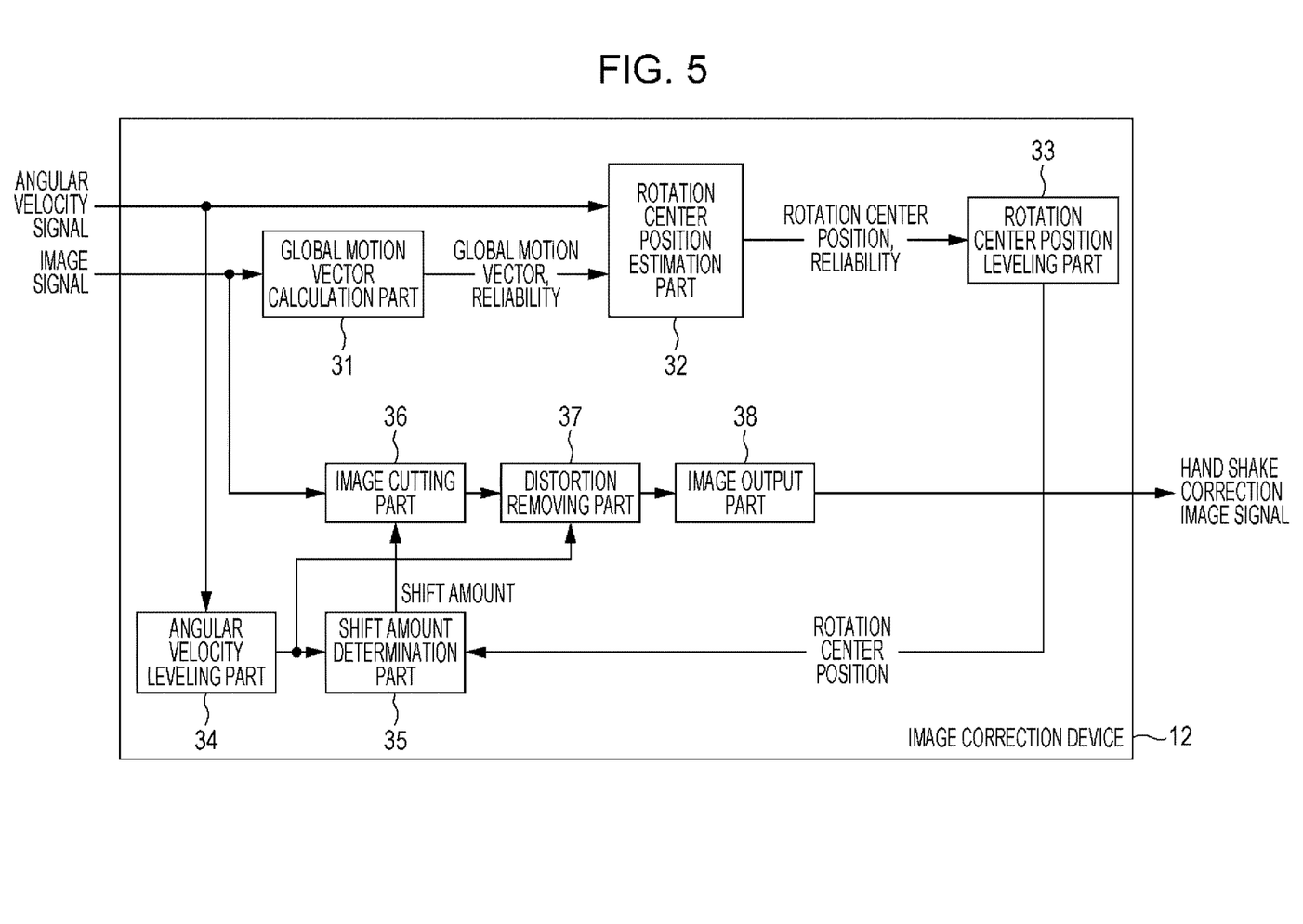
FIG. 5 is a block diagram showing an example of a configuration of the image correction device.

FIG. 5 shows an example of a configuration of the image correction device 12. The image correction device 12 includes a global motion vector calculation part 31, a rotation center position estimation part 32, a rotation center position leveling part 33, an angular velocity leveling part 34, a shift amount determination part 35, an image cutting part 36, a distortion removing part 37, and an image output part 38.

The global motion vector calculation part 31 calculates, based on an image signal of a predetermined frame rate input from the image taking part 25 of the endoscopic device 11, a motion vector of the whole image (hereinafter, referred to as a global motion vector) and a reliability thereof, and outputs the result of the calculation to the rotation center position estimation part 32.

Figure 6:
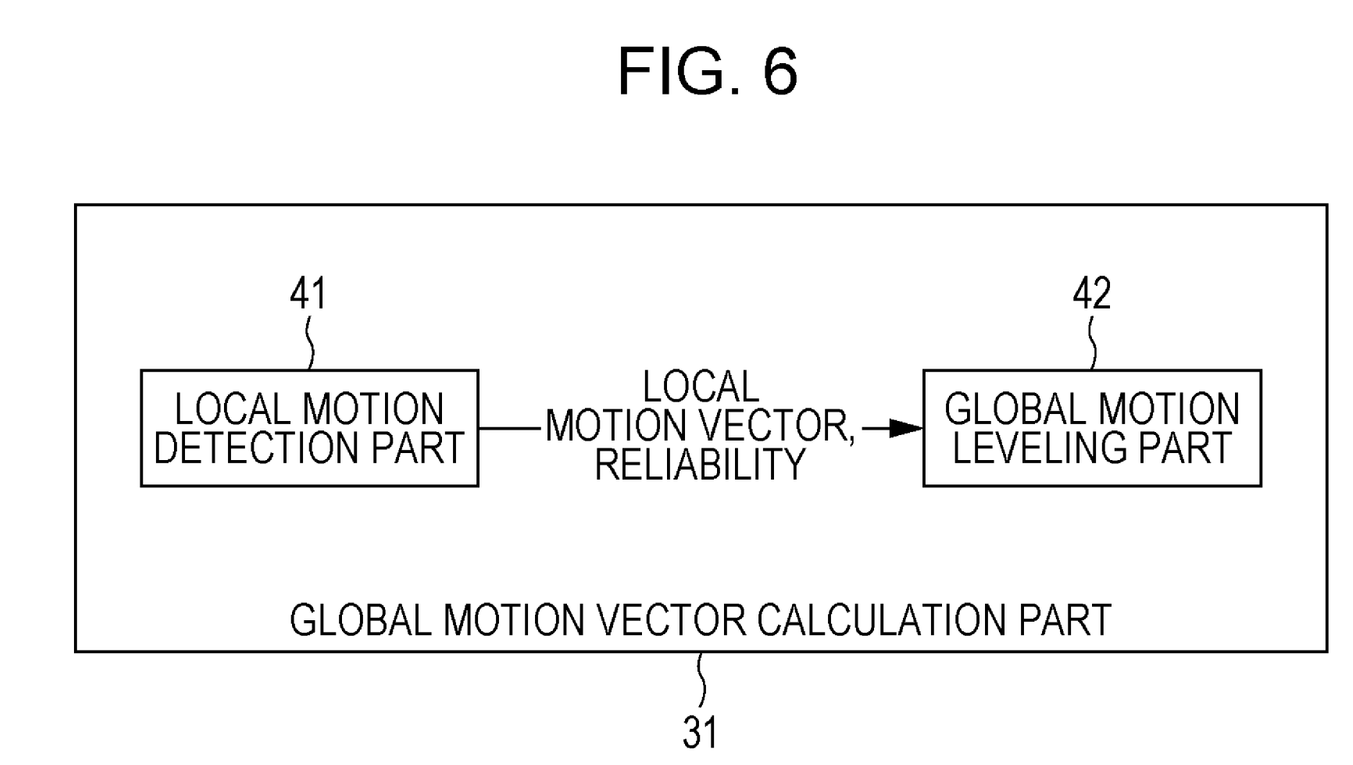
FIG. 6 is a block diagram showing an example of a configuration of a global motion vector calculation part.

FIG. 6 shows an example of a configuration of the global motion vector calculation part 31. The global motion vector calculation part 31 includes a local motion detection part 41 and a global motion leveling part 42.

The local motion detection part 41 divides an image of an image signal input from the image taking part 25 into blocks having a predetermined size and performs comparison with an image signal before one frame per block to output a motion vector in a block unit (hereinafter, also referred to as a local motion vector) and a reliability thereof to the global motion leveling part 42.

The global motion leveling part 42 integrates a high-reliability local motion vector among the local motion vectors of the blocks of the respective frames to determine a global motion vector of the corresponding frame. Furthermore, the global motion leveling part 42 removes an instantaneous error by leveling global motion vectors of several frames before the corresponding frame. When a frequency of estimation of a rotation center position in the downstream rotation center position estimation part 32 is lower than the frame rate of the image signal, the leveling may be performed using the global motion vectors of several frames after the corresponding frame together.

Returning to FIG. 5, the rotation center position estimation part 32 estimates, based on the angular velocity of the head part 24 detected by the gyro part 26 of the endoscopic device 11, the global motion vector, and the reliability thereof, the position of the rotation center (support) at the time when the objective lens 22 is moved by moving the head part 24 of the endoscopic device 11, and outputs the result of the estimation with a reliability thereof to the rotation center position leveling part 33. The rotation center position is continuously estimated at predetermined time intervals.

The rotation center position leveling part 33 performs leveling by integrating the estimated rotation center position in a time direction, and outputs, to the shift amount determination part 35, the rotation center position from which the instantaneous error has been removed.

The angular velocity leveling part 34 performs leveling by integrating the angular velocity of the head part 24 detected by the gyro part 26 of the endoscopic device 11 in the time direction, and outputs, to the shift amount determination part 35 and the distortion removing part 37, the angular velocity from which the instantaneous error has been removed.

The shift amount determination part 35 calculates a moving amount of the objective lens 22 based on the leveled rotation center position and the leveled angular velocity, determines a shift amount of the image cutting area from the calculated moving amount of the objective lens 22, and notifies the image cutting part 36 of the result of the determination. The shift amount of the image cutting area corresponding to the moving amount of the objective lens 22 varies with the magnification of the objective lens 22. Therefore, in the shift amount determination part 35, a function for calculating the shift amount from the magnification and the moving amount of the objective lens 22 is held, or a table indicating the correspondence between these elements is previously held.

The image cutting part 36 cuts the pixels of the cutting area, of which the position is adjusted according to the shift amount from the shift amount determination part 35, from an image signal of a predetermined frame rate sequentially input from the image taking part 25 of the endoscopic device 11, and outputs, to the distortion removing part 37, a hand shake correction image signal obtained as a result.

When a rolling shutter distortion (which may occur when the shutter mechanism of the image taking part 25 is a rolling shutter) occurs in the hand shake correction image signal from the image cutting part 36, the distortion removing part 37 removes the distortion to output the resulting signal to the image output part 38. An existing arbitrary method may be applied to remove the rolling shutter distortion.

The image output part 38 outputs, to the downstream (in this case, the display device 13), the hand shake correction image signal input through the distortion removing part 37.

Next, the estimation of the rotation center position and the shift amount of the position of the cutting area will be described in detail with reference to FIGS. 7 and 8.

Figure 7:
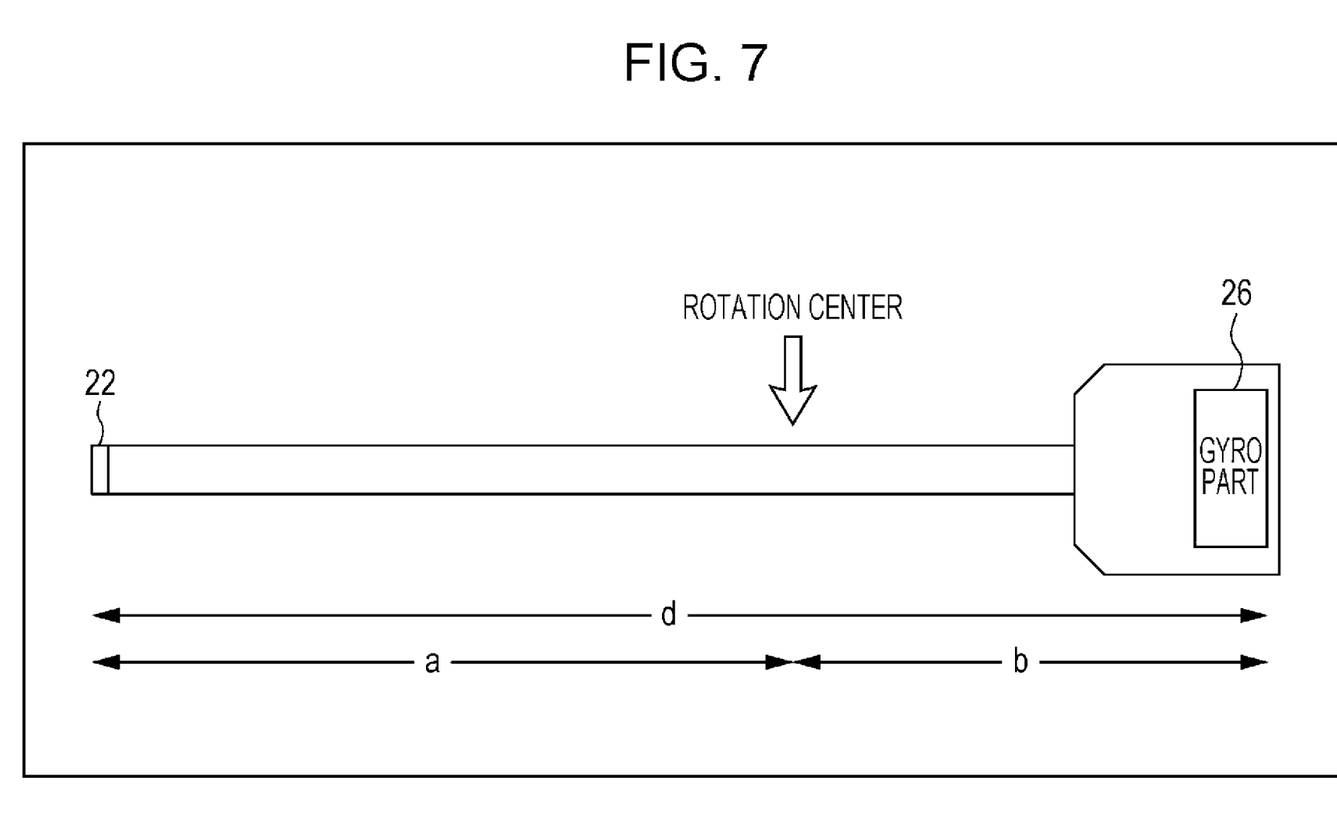
FIG. 7 is a diagram showing a positional relationship between an objective lens, a rotation center, and a gyro part in the endoscopic device.
Figure 8:
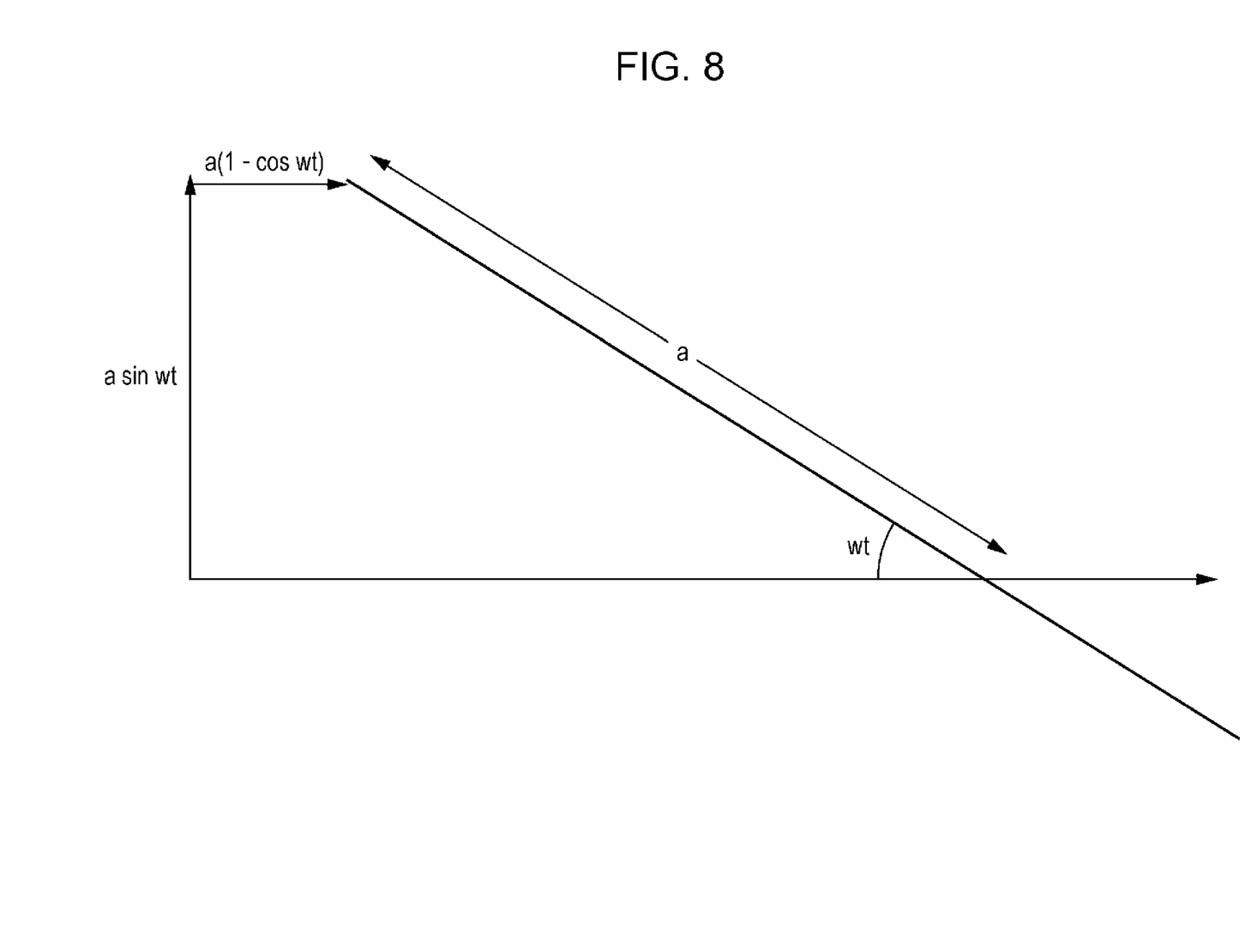
FIG. 8 is a diagram showing a relationship between an angular velocity of the gyro part and a moving amount of the objective lens.

FIG. 7 shows a relationship between the objective lens 22 of the endoscopic device 11, the gyro part 26, and the rotation center position. FIG. 8 shows a relationship between the moving amount of the objective lens 22 and the angular velocity of the gyro part 26.

As shown in FIG. 7, a distance between the objective lens 22 and the gyro part 26 is represented by d, a distance between the objective lens 22 and the rotation center is represented by a, and a distance between the rotation center and the gyro part 26 is represented by b. When the endoscopic device 11 is used in a laparoscopic operation in the state shown in FIG. 1, the trocar 2 becomes a rotation center.

The relationship between the moving amount (Dx, Dy, Dz) of the objective lens 22 and the angular velocity (Yaw angular velocity $w_y$, Pitch angular velocity $w_p$) of the gyro part 26 is as the following expression (1) (approximate expression).

$$Dx = a \text{ degree } \sin(w_y t)$$

$$Dy = a \text{ degree } \sin(w_p t)$$

$$Dz = a(1-\cos(w_y t))(1-\cos(w_p t)) \quad (1)$$

t represents a one-frame time.

In addition, the relationship between the detected global motion vector (Vx, Vy) and the angular velocity (Yaw angular velocity $w_y$, Pitch angular velocity $w_p$) of the gyro part 26 is as the following expression (2) (approximate expression).

$$Vx = a \text{ degree } \sin(w_y t)$$

$$Vy = a \text{ degree } \sin(w_p t) \quad (2)$$

t represents a one-frame time.

In the rotation center position estimation part 32, the sequentially input angular velocity and the leveled global motion vector are applied to the expression (2) to calculate a value of the position a of the rotation center.

In the shift amount determination part 35, the leveled rotation center position a and the leveled angular velocity are applied to the expression (1) to calculate the moving amounts Dx, Dy, and Dz of the objective lens 22 and to determine a shift amount of the cutting area based on these moving amounts.

(Description of Operation)

Figure 9:
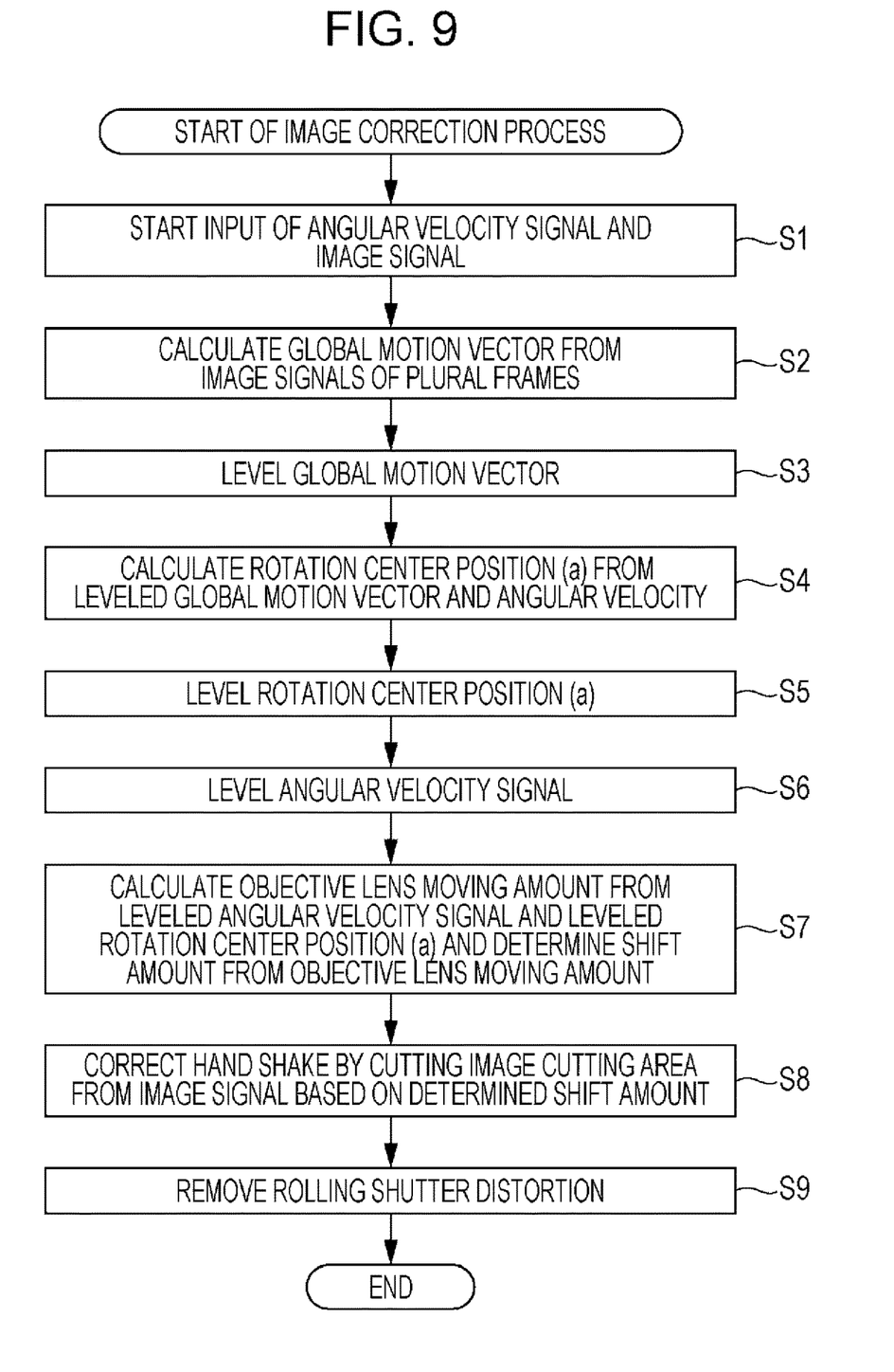
FIG. 9 is a flowchart illustrating the image correction process.

Next, FIG. 9 is a flowchart illustrating the image correction process of the image correction device 12.

In Step S1, the input of an image signal of a predetermined frame rate and the input of an angular velocity signal indicating the motion of the head part 24 are started from the endoscopic device 11 to the image correction device 12. The image signal is input to the global motion vector calculation part 31 and the image cutting part 36, and the angular velocity signal is input to the rotation center position estimation part 32 and the angular velocity leveling part 34.

In Step S2, in the global motion vector calculation part 31, the local motion detection part 41 divides an image of an image signal input from the upstream into blocks having a predetermined size and performs comparison with an image signal before one frame per block to calculate a local motion vector in a block unit and a reliability thereof. In Step S3, the global motion leveling part 42 of the global motion vector calculation part 31 integrates a high-reliability local motion vector among the local motion vectors of the blocks of the respective frames to determine a global motion vector of the corresponding frame, and levels global motion vectors of several frames before the corresponding frame to output the result of the leveling to the rotation center position estimation part 32.

In Step S4, in the rotation center position estimation part 32, the sequentially input angular velocity and the leveled global motion vector are applied to the expression (2) to calculate a value of the position a of the rotation center. In Step S5, the rotation center position leveling part 33 performs leveling by integrating the estimated rotation center position in the time direction, and outputs the result of the leveling to the shift amount determination part 35.

In the angular velocity leveling part 34, in Step S6, the leveling is performed by integrating the angular velocity of the head part 24 detected by the gyro part 26 of the endoscopic device 11 in the time direction, and the result of the leveling is output to the shift amount determination part 35 and the distortion removing part 37. In Step S7, the shift amount determination part 35 calculates the moving amount of the objective lens 22 based on the leveled rotation center position and the leveled angular velocity, and determines a shift amount of the image cutting area from the calculated moving amount of the objective lens 22 to notify the image cutting part 36 of the result of the determination.

In Step S8, the image cutting part 36 cuts the pixels of the cutting area, of which the position is adjusted according to the shift amount from the shift amount determination part 35, from the image signal of a predetermined frame rate sequentially input from the endoscopic device 11, and outputs, to the distortion removing part 37, a hand shake correction image signal obtained as a result.

In Step S9, when a rolling shutter distortion occurs in the hand shake correction image signal from the image cutting part 36, the distortion removing part 37 removes the distortion to output the resulting signal to the image output part 38. The image output part 38 outputs, to the display device 13, the hand shake correction image signal input through the distortion removing part 37. The description of the image correction process is finished.

As described above, the endoscopic system 10 according to this embodiment can correct hand shake which may occur in a video image taken by the endoscopic device 11.

In addition, the endoscopic system 10 according to this embodiment can notify a user such as a doctor of, for example, the value of the the estimated position a of the rotation center (trocar). Accordingly, the user can grasp the length of the part which is inserted into the abdominal cavity.

In addition, for example, when a 3D measurement functions is applied to the endoscopic device 11, the positional relationship between the affected part which is a subject and the rotation center (trocar) can be easily calculated.

Figure 10:
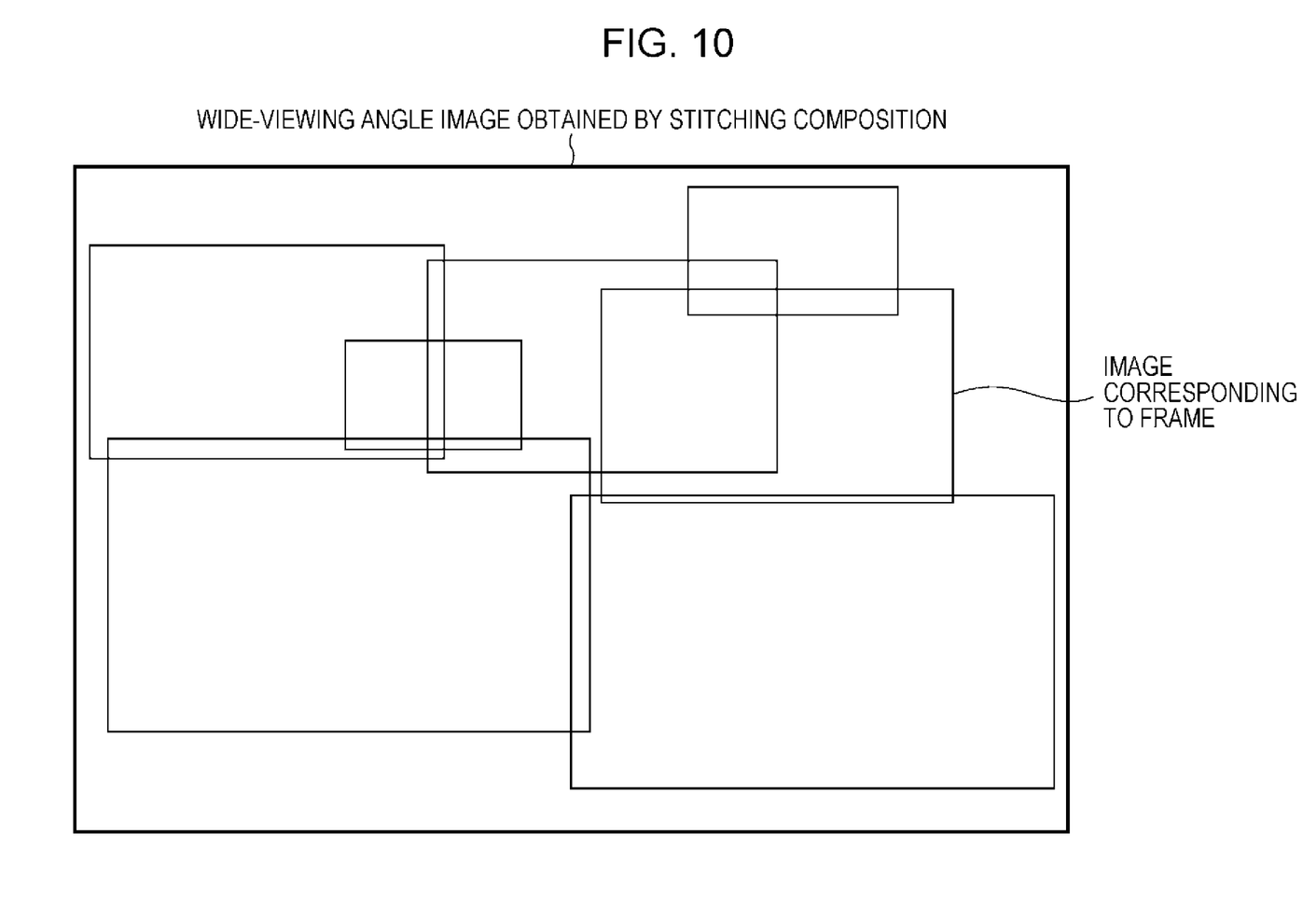
FIG. 10 is a diagram illustrating stitching composition using an image after hand shake correction.

Furthermore, for example, when a plurality of images obtained as a result of taking the images by moving the endoscopic device 11 with the trocar acting as a rotation center are subjected to stitching composition based on the rotation center position and the angular velocity as shown in FIG. 10, a wide-viewing angle image with high accuracy can be obtained with a relatively small processing amount.

The above-described series of processes of the image correction device 12 can be executed by hardware or software. When executing the series of processes by software, a program constituting the software is installed in a computer. Here, the computer includes a computer incorporated in dedicated hardware, and a computer such as a general-purpose personal computer which can execute various functions through installation of various programs.

Figure 11:
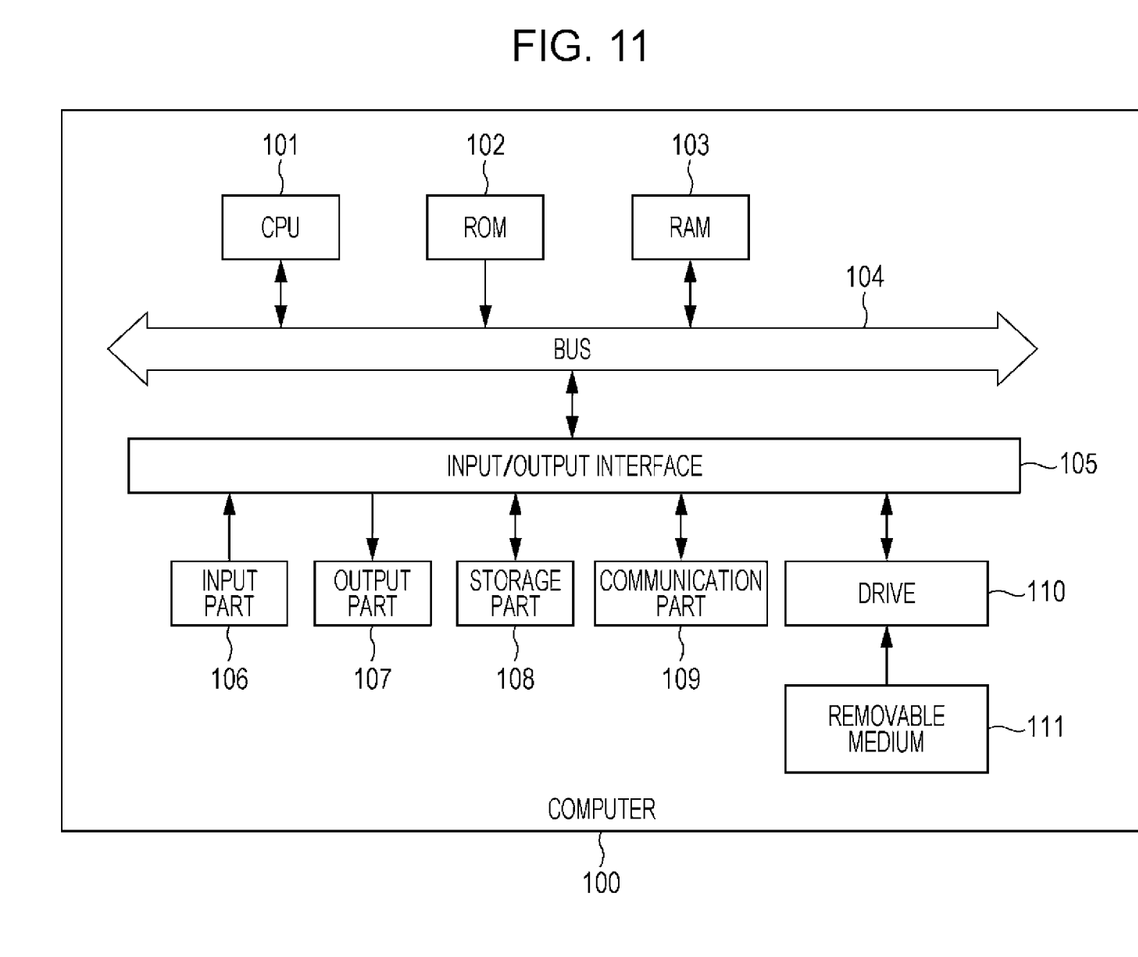
FIG. 11 is a block diagram showing an example of a configuration of a computer.

FIG. 11 is a block diagram showing an example of a configuration of hardware of the computer which executes the above-described series of processes using a program.

In a computer 100, a central processing unit (CPU) 101, a read only memory (ROM) 102, and a random access memory (RAM) 103 are connected to each other through a bus 104.

Furthermore, an input/output interface 105 is connected to the bus 104. An input part 106, an output part 107, a storage part 108, a communication part 109, and a drive 110 are connected to the input/output interface 105.

The input part 106 is composed of a keyboard, a mouse, a microphone, or the like. The output part 107 is composed of a display, a speaker, or the like. The storage part 108 is composed of a hard disk, a nonvolatile memory, or the like. The communication part 109 is composed of a network interface or the like. The drive 110 drives a removable medium 111 such as a magnetic disk, an optical disk, a magneto-optical disk, or a semiconductor memory.

In the computer 100 configured as described above, the CPU 101 executes, for example, a program stored in the storage part 108 by loading the program to the RAM 103 through the input/output interface 105 and the bus 104, and thus the above-described series of processes are performed.

The program which is executed by the computer 100 (CPU 101) can be provided by being recorded on, for example, the removable medium 111 as a package medium or the like. In addition, the program can be provided through a wired or wireless transmission medium such as local area network, the Internet, or digital satellite broadcasting.

The program which is executed by the computer 100 may be a program for performing the processes chronologically along the order described in the present description, or a program for performing the processes in parallel or at necessary timings such as when there is a call.

The embodiments of the present disclosure are not limited to the above-described embodiments, and various modifications can be made without departing from the gist of the present disclosure.

Further, the present technology may employ the following configurations.

(1) An image processing device that processes images obtained by an endoscopic device including: circuitry configured to estimate an approximate center of rotation of the endoscopic device based on motion detection in response to a movement of an objective lens at a distal portion of the endoscopic device by manipulating a proximal portion of the endoscopic device.

(2) The image processing device of (1), wherein the motion detection includes determining an angular velocity.

(3) The image processing device of any of (1) to (2), wherein determining the motion detection includes analysis of relative motion of multiple images obtained by the endoscopic device.

(4) The image processing device of (3), wherein the analysis of relative motion of multiple images includes determining a motion vector of whole images obtained by the objective lens.

(5) The image processing device of any of (1) to (4), wherein the motion detection includes obtaining an angular velocity of the proximal portion of the endoscopic device.

(6) The image processing device of (5), wherein the angular velocity of the proximal portion of the endoscopic device is detected by a motion sensor at the proximal portion of the endoscopic device.

(7) The image processing device of any of (1) to (6), wherein the circuitry removes instantaneous error values in the estimated approximate center of rotation based on an integration of estimated approximate center of rotation values over time.

(8) The image processing device of (2), wherein the circuitry removes instantaneous error values in the angular velocity based on an integration of detected angular velocity values over time.

(9) The image processing device of any of (1) to (8), wherein the circuitry removes rolling shutter distortion in images obtained by the endoscopic device.

(10) The image processing device of any of (1) to (9), wherein the circuitry corrects hand shake in images obtained by the endoscopic device based on the approximate center of rotation of the endoscopic device.

(11) The image processing device of any of (1) to (10), wherein the circuitry combines a plurality of images obtained by moving the endoscopic device based on the approximate center of rotation of the endoscopic device.

(12) The image processing device of any of (1) to (11), wherein the circuitry determines a length of insertion of the treatment device based on the approximate center of rotation of the endoscopic device.

(13) The image processing device of any of (1) to (12), wherein the circuitry determines a positional relationship between a target treatment site and the treatment device based on the approximate center of rotation of the endoscopic device.

(14) An endoscopic system, including: an endoscopic device that includes an objective lens at a distal portion thereof; and an image processing device that includes circuitry configured to estimate an approximate center of rotation of the endoscopic device based on motion detection in response to a movement of an objective lens at a distal portion of the endoscopic device by manipulating a proximal portion of the endoscopic device.

(15) The endoscopic system of (14), wherein the motion detection includes determining an angular velocity.

(16) The endoscopic system of any of (14) to (15), wherein determining the motion detection includes analysis of relative motion of multiple images obtained by the endoscopic device.

(17) The endoscopic system of any of (14) to (16), wherein the image processing device corrects hand shake in images obtained by the endoscopic device.

(18) The endoscopic system of any of (14) to (17), wherein the image processing device produces a wide-viewing angle image by combining a plurality of images based on the approximate center of rotation of the endoscopic device.

(19) The endoscopic system of (18), wherein the image processing device produces the wide-viewing angle image by combining the plurality of images based on a detected angular velocity of the endoscopic device.

(20) The endoscopic system of any of (14) to (19), wherein the endoscopic device is a rigid endoscope.

(21) A method of processing images obtained by an endoscopic device, comprising: estimating, based on motion detection, an approximate center of rotation of the endoscopic device in response to a movement of an objective lens at a distal portion of the endoscopic device by manipulating a proximal portion of the endoscopic device.

(22) An method of performing a laparoscopic procedure, comprising: inserting a treatment device through a trocar positioned in a patient; and obtaining, based on motion detection, information regarding an approximate center of rotation of the treatment device in response to a movement of an objective lens at a distal portion of the endoscopic device by manipulating a proximal portion of the endoscopic device.

(23) The method of performing a laparoscopic procedure according to (22), wherein the treatment device is a rigid endoscope.

(24) The method of performing a laparoscopic procedure according to any of (22) to (23), further including determining a length of insertion of the treatment device based on the approximate center of rotation.

(25) The method of performing a laparoscopic procedure according to any of (22) to (24), further comprising determining a positional relationship between a target treatment site and the treatment device based on the approximate center of rotation.

(26) The method of performing a laparoscopic procedure according to (25), wherein the determining the positional relationship between the target treatment site and the treatment device includes measuring the target treatment site in three dimensions.

(27) An endoscopic system includes: an endoscopic device in which an objective lens is provided at a tip end of an insertion part which is inserted into a body cavity, a head part is provided at a base end, and a gyro part which detects a moving angular velocity of the head part is provided in the head part; and an image processing device including a global motion calculation part which calculates, from an image signal which is input from the endoscopic device and corresponds to an optical image converged by the objective lens, a motion of the entire image corresponding to the image signal, and an estimation part which estimates, based on the calculated motion of the entire image and the detected angular velocity, a position of a rotation center when the objective lens is moved according to the motion of the head part.

(28) The endoscopic system according to (27), in which the image processing device is further provided with a correction part which corrects hand shake of the image signal by cutting a cutting area from an effective pixel area of the image signal input from the endoscopic device, and the cutting area is determined based on the estimated position of the rotation center and the detected angular velocity.

(29) The endoscopic system according to (27) or (28), in which the image processing device is further provided with an objective lens moving amount calculation part which calculates a moving amount of the objective lens based on the estimated position of the rotation center and the detected angular velocity.

(30) The endoscopic system according to (29), in which the objective lens moving amount calculation part further determines a shift amount of the cutting area based on the calculated moving amount of the objective lens, and the correction part corrects the hand shake of the image signal by adjusting a position of the cutting area according to the determined shift amount.

(31) The endoscopic system according to any one of (28) to (30), in which the correction part corrects the hand shake of each image signal input at a predetermined frame rate from the endoscopic device, and the estimation part estimates the position of the rotation center at a frequency which is equal to or lower than the predetermined frame rate.

(32) The endoscopic system according to any one of (27) to (31), in which the image processing device is further provided with a rotation center position leveling part which levels the estimated position of the rotation center in a time direction.

(33) The endoscopic system according to any one of (27) to (32), in which the image processing device is further provided with an angular velocity leveling part which levels the detected angular velocity in a time direction.

(34) The endoscopic system according to any one of (28) to (33), in which the image processing device is further provided with a distortion removing part which removes a rolling shutter distortion of the image signal subjected to the hand shake correction.

(35) An image processing device includes: a global motion calculation part which calculates, from an image signal which is input from an endoscopic device in which an objective lens is provided at a tip end of an insertion part which is inserted into a body cavity, a head part is provided at a base end, and a gyro part which detects a moving angular velocity of the head part is provided in the head part, and corresponds to an optical image converged by the objective lens, a motion of the entire image corresponding to the image signal; and an estimation part which estimates, based on the calculated motion of the entire image and the angular velocity input from the endoscopic device, a position of a rotation center when the objective lens is moved according to the motion of the head part.

(36) An image processing method which is performed by an image processing device which processes an image signal which is input from an endoscopic device in which an objective lens is provided at a tip end of an insertion part which is inserted into a body cavity, a head part is provided at a base end, and a gyro part which detects a moving angular velocity of the head part is provided in the head part, and corresponds to an optical image converged by the objective lens, includes: calculating a motion of the entire image corresponding to the image signal; and estimating, based on the calculated motion of the entire image and the angular velocity input from the endoscopic device, a position of a rotation center when the objective lens is moved according to the motion of the head part.

(37) A program which causes a computer to function as: a global motion calculation part which calculates, from an image signal which is input from an endoscopic device in which an objective lens is provided at a tip end of an insertion part which is inserted into a body cavity, a head part is provided at a base end, and a gyro part which detects a moving angular velocity of the head part is provided in the head part, and corresponds to an optical image converged by the objective lens, a motion of the entire image corresponding to the image signal; and an estimation part which estimates, based on the calculated motion of the entire image and the angular velocity input from the endoscopic device, a position of a rotation center when the objective lens is moved according to the motion of the head part.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

2 Trocar
10 Endoscopic system
11 Endoscopic device
12 Image correction device
13 Display device
21 Tube part
22 Objective lens
23 Optical lens part
24 Head part
25 Image taking part
26 Gyro part
31 Global motion vector calculation part
32 Rotation center position estimation part
33 Rotation center position leveling part
34 Angular velocity leveling Part
35 Shift amount determination part
36 Image cutting part
37 Distortion removing part
38 Image output part
41 Local motion detection part
42 Global motion leveling part
100 Computer
101 CPU

The invention claimed is:

1. A medical system, comprising:
an endoscopic device including a head portion and an insert portion with an objective lens, the insert portion coupled to the head portion; and
an image processing device including circuitry configured to
obtain an angular velocity of the head portion of the endoscopic device and an image signal generated by the endoscopic device;
detect a motion based on the image signal corresponding to a movement of the endoscopic device;
estimate a center of rotation of the endoscopic device in the insert portion based on the motion and the angular velocity, the estimated center of rotation being on the endoscope;
calculate a shift amount of the objective lens in the insert portion based on the estimated center of rotation in the insert portion and the angular velocity; and
correct a hand shake in the image signal based on the estimated center of rotation of the endoscopic device by moving a position of a cutting area by the shift amount, wherein the insert portion is a tube of the endoscope.

2. The medical system of claim 1, further comprising:
a motion sensor at the head portion of the endoscopic device to detect the angular velocity of the head portion of the endoscopic device.

3. The medical system of claim 1, wherein the circuitry is configured to obtain a leveled center of rotation by removing instantaneous error values in the estimated center of rotation based on an integration of estimated center of rotation values over time.

4. The medical system of claim 1, wherein the circuitry is configured to obtain a leveled angular velocity by removing instantaneous error values in the angular velocity based on an integration of detected angular velocity values over time.

5. The medical system of claim 1, wherein the circuitry combines a plurality of images obtained by moving the endoscopic device based on the approximate center of rotation of the endoscopic device.

6. The medical system of claim 3, wherein the circuitry is further configured to calculate the shift amount of the objective lens based on the leveled estimated center of rotation and the angular velocity.

7. The medical system image of claim 4, wherein the circuitry is further configured to calculate the shift amount of the objective lens based on the estimated center of rotation and the leveled angular velocity.

8. The medical system image of claim 1, wherein the circuitry is further configured to
divide one of the images into blocks, the one of the images being obtained by the objective lens on the endoscopic device in response to the movement of the endoscopic device;
generate a plurality of local motion vectors based on a comparison of each of the blocks with a respective block of an image signal of a previous frame; and
determine a global motion vector of the one of the images by integrating the plurality of local motion vectors.

9. The medical system of claim 8, wherein the circuitry is further configured to determine the global motion vector of the one of the images by integrating one or more local motion vectors with a high reliability among the plurality of local motion vectors.

10. The medical system image of claim 1, wherein the circuitry is further configured to cut, from an entire pixel area of the image signal, the cutting area having a smaller size than the entire pixel area.

* * * * *